(12) United States Patent
Parton et al.

(10) Patent No.: US 8,772,550 B2
(45) Date of Patent: Jul. 8, 2014

(54) CATALYSED PHENOL HYDROGENATION

(75) Inventors: Rudy Francois Maria Jozef Parton, Winksele (BE); Johan Thomas Tinge, Sittard (NL); Bert Hoeksema, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 73 days.

(21) Appl. No.: 13/516,897

(22) PCT Filed: Dec. 15, 2010

(86) PCT No.: PCT/EP2010/069707
§ 371 (c)(1),
(2), (4) Date: Aug. 28, 2012

(87) PCT Pub. No.: WO2011/073233
PCT Pub. Date: Jun. 23, 2011

(65) Prior Publication Data
US 2012/0323042 A1    Dec. 20, 2012

(30) Foreign Application Priority Data
Dec. 18, 2009   (EP) .................................... 09179894

(51) Int. Cl.
*C07C 45/62*   (2006.01)
*C07C 29/20*   (2006.01)

(52) U.S. Cl.
USPC ......................................... 568/362; 568/835

(58) Field of Classification Search
USPC ................................................ 568/362, 835
See application file for complete search history.

(56) References Cited

U.S. PATENT DOCUMENTS 3,998,884 A    12/1976   Gibson

FOREIGN PATENT DOCUMENTS

DE    197 27 712    1/1999
EP    1 050 339    11/2000

OTHER PUBLICATIONS

International Search Report for PCT/EP2010/069707, mailed Mar. 31, 2011.
Written Opinion of the International Searching Authority for PCT/EP2010/069707, mailed Mar. 31, 2011.
CRC Handbook of Chemistry and Physics, 74th edition (1993-1994), David R. Lide (Editor-in-Chief), CRC Press, ISBN-0/8493-0474-1, section 4, pp. 35, 78, 80, 85, 86, 97 and 99.

*Primary Examiner* — Sikarl Witherspoon
(74) *Attorney, Agent, or Firm* — Nixon & Vanderhye P.C.

(57) ABSTRACT

The invention relates to a method for hydrogenating an aromatic compound. The invention in particular relates to a method for preparing cyclohexanone, cyclohexanol or a mixture thereof in a continuous way by catalytically hydrogenating phenol fed into a reactor comprising a supported hydrogenation catalyst, comprising a dopant selected from the group of alkali metal hydroxides, alkaline earth metal hydroxides, alkaline earth metal oxides, carbonates of alkali metals and carbonates of alkaline earth metals, and in which process during the hydrogenation of phenol continuously or intermittently water is fed into the reactor, the weight to weight ratio of water fed into the reactor to phenol fed into the reactor on average being 0.1 or less.

16 Claims, No Drawings

CATALYSED PHENOL HYDROGENATION

This application is the U.S. national phase of International Application No. PCT/EP2010/069707, filed 15 Dec. 2010, which designated the U.S. and claims priority to EP Application No. 09179894.2, filed 18 Dec. 2009, the entire contents of each of which are hereby incorporated by reference.

The invention relates to a method for hydrogenating an aromatic compound. The invention in particular relates to a method for preparing cyclohexanone, cyclohexanol or a mixture thereof in a continuous process by hydrogenation of phenol.

Cyclohexanone can be employed as an industrial solvent or as an activator in oxidation reactions. It is also used as in intermediate, inter alia in the production of adipic acid, cyclohexanone resins, caprolactam, nylon 6 and nylon 6,6.

In the preparation of cyclohexanone from phenol, usually also cyclohexanol (which can be considered an intermediate product useful for further conversion to cyclohexanone) is formed.

Cyclohexanone and/or cyclohexanol can be conventionally prepared from phenol by catalytic hydrogenation in a phenol hydrogenation reactor, e.g. using a platinum or a palladium catalyst. The reaction can be carried out in the liquid phase or the vapour phase. [Kirk-Othmer Encyclopedia of Chemical Technology, e.g. $3^{rd}$ Edition, Vol 7 (1979) page 410-416; I. Dodgson et al. "A low Cost Phenol to Cyclohexanone Process", Chemistry & Industry 18 Dec. 1989, p 830-833; A. C. Dimian and C. S. Bildea "Chemical Process Design, Computer-Aided Case Studies", Wiley-VCH Verlag GmbH&Co. KGaA, Weinheim, Germany, Chapter 5, page 129-172; or M. T. Musser "cyclohexanol and Cyclohexanone", Ullmann's Encyclopedia of Industrial Chemistry ($7^{th}$ Edition, 2007), electronically available via http://www.mrw.interscience.wiley.com/emrw/9783527306732/search/firstpage (hereafter "Musser")].

In conventional processes generally a compromise has to be made between yield of the desired product (cyclohexanone and/or cyclohexanol formed as a percentage of the phenol feed), the selectivity of the reaction (cyclohexanone and/or cyclohexanol formed as a percentage of phenol that has been converted). As described in the above identified handbooks several factors play a role herein, including temperature, choice of catalyst, and the hydrogen/phenol feed ratio.

It is an objective of the present invention to provide a novel method for preparing a desired compound by catalytically hydrogenating an aromatic compound, in particular phenol, into one or more hydrogenated compounds, in particular cyclohexanone, cyclohexanol or a mixture thereof.

It is in particular an objective to provide such a method which allows an increased conversion of the aromatic compound, in particular phenol, and/or an increased selectivity towards the formation of one or more desired compounds, in particular cyclohexanone and/or cyclohexanol.

It has now been found that one or more objectives underlying the invention are met by using a specific aid, which may be contacted with the catalyst prior to and/or during the hydrogenation of phenol.

Accordingly, in a first aspect, the present invention relates to a method for preparing cyclohexanone, cyclohexanol or a mixture thereof in a continuous process, comprising catalytically hydrogenating phenol fed into a reactor comprising a hydrogenation catalyst, in which method the hydrogenation catalyst is a supported catalyst, comprising a dopant selected from the group of alkali metal hydroxides, alkaline earth metal hydroxides, alkaline earth metal oxides, carbonates of alkali metals and carbonates of alkaline earth metals; and wherein during the hydrogenation of phenol continuously or intermittently water is fed into the reactor, the weight to weight ratio of water fed into the reactor to phenol fed into the reactor on average being 0.1 or less.

The hydrogenation catalyst may in principle be any supported hydrogenation catalyst capable of catalysing the hydrogenation of the compound to be hydrogenated.

Usually, the catalyst comprises one or more catalytically active metals. Such metal or metals may in particular be selected from the group of palladium, platinum, ruthenium, rhodium, iridium, rubidium and osmium.

Palladium, platinum or a combination thereof are preferred catalytically active metals, in particular for the hydrogenation of phenol, especially for the hydrogenation into cyclohexanone or a mixture of cyclohexanone and cyclohexanol, wherein the cyclohexanone is the major component of these two.

In principle any support may be used suitable for use in the hydrogenation of the compound of interest in combination with the catalytic material it supports. Suitable supports in particular may be selected from the group of alumina, activated carbon, titanium oxide, calcium carbonate and carbon black. Another support that may be used is silica.

In particular preferred for a good stability of the support under reaction conditions and/or an improved conversion is a support selected from the group of alumina and activated carbon.

Alumina is in particular preferred for an embodiment wherein water and the compound to be hydrogenated are fed into the reactor as a vapour.

Activated carbon is in particular preferred for en embodiment wherein water and compound to be hydrogenated are fed into the reactor as a liquid.

As illustrated by the Examples, below, treating a hydrogenation catalyst with water by continuously or intermittently feeding water (or steam) during the hydrogenation reaction, results in an increased conversion of phenol. Although the conversion is maintained at a higher level when water is continuously added, the inventors have observed that also when the water feed is stopped and the hydrogenation of phenol is continued, a higher conversion is observed than in a reference method, wherein no water has been fed into the reactor at all. This is in particular important if the feeding of water is done intermittently.

It is further envisaged that water may also be used to improve a method for preparing one or more compounds other than cyclohexanol or cyclohexanone by hydrogenation of an aromatic compound other than phenol. Accordingly, the present invention further relates to a method for catalytically hydrogenating an aromatic compound fed into a reactor comprising a hydrogenation catalyst, in a continuous process, to which reactor continuously or intermittently water is fed.

Besides for the hydrogenation of phenol, it is envisaged that such method may be used for the hydrogenation of a functional group, e.g. hydroxyl, carbonyl, nitro, carboxyl or an unsaturated carbon-carbon bond, such as an unsaturated carbon-carbon bond of 1-oxo-2-propenyl (CH=CH—(C=O)—) or of another aromatic compound comprising a substituent, in particular for hydrogenating a functional group of a substituted benzene into a corresponding hydrogenated compound, such as for the hydrogenation of nitrobenzene into aniline.

Further, it is envisaged that such method may be used for the hydrogenation of an aromatic compound, comprising an aromatic ring, into a corresponding cyclo-aliphatic compound, such as for the hydrogenation of benzene into cyclohexane, or for the hydrogenation of aniline into cyclohexylamine.

Compounds thus prepared may for instance be used as a solvent or as intermediate for another desired compound. For instance, cyclohexane may be oxidised to prepare cyclohexanone.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included. Thus, when referring to a specific noun, e.g. "compound", this means "at least one" thereof, e.g. "at least one compound", unless specified otherwise.

It is noticed that DE-19727712 discloses a hydrogenation process, which is performed batchwise and wherein use is made of a wet catalyst that is fed into the reactor after mixing it with an alkaline component comprising from 20 wt. % to 200 wt. % of water relative to the alkaline component. This document, however, does not disclose or suggest the continuous or intermittent feeding of water during the course of the hydrogenation reaction that is performed in a continuous mode.

Further, it is noted that U.S. Pat. No. 3,998,884 discloses hydrogenation of phenol, predominantly into cyclohexanol, by using a nickel on aluminium oxide catalyst and controlled amounts of hydrogen and/or water in the reaction mixture used. The amounts of water used in said reference, however, are much higher than the amounts according to the present invention and with many other catalysts. None of these prior art references, nor their combination, teaches or suggests the processes of the present invention and the merits thereof.

The hydrogenation reactor may in particular be any type of reactor suitable for hydrogenation of the compound to be hydrogenated, in particular any reactor suitable for the hydrogenation of phenol. In particular, the reactor may be selected from packed bed reactors, slurry reactors, shell and tubes heat exchange reactors with catalyst in tubes and with generation of steam, and any other suitable type of reactor. Most preferably, the hydrogenation according to the invention is carried out in a shell and tubes heat exchange reactor.

When referring herein to water being fed into the reactor, the water can in principle be in any form; in particular water can be fed into the reactor as a fluid comprising water. The fluid can be a vapour, such as steam or a mixture comprising water vapour and a gas, such as hydrogen, a mixture comprising water vapour and phenol vapour or a vapour of another compound to be hydrogenated; the fluid can be a liquid, such as liquid water or an aqueous liquid, or a mixture comprising liquid water and liquid phenol or other liquid compound to be hydrogenated; or the fluid can be a mixture of a vapour and a liquid.

In a specific embodiment phenol (or other compound to be hydrogenated) and water are fed into the reactor as a vapour. For such a method, in particular good results have been achieved with a packed bed reactor.

In a further specific embodiment phenol (or other compound to be hydrogenated) and water fed into the reactor as a liquid.

The water is typically fed into the hydrogenation reaction providing a weight to weight ratio of water to the compound to be hydrogenated (in particular phenol) that on average is 0.1 or less. Without being bound by theory it is believed that there is no additional beneficial effect with respect to increasing the conversion of the compound to be hydrogenated, under otherwise the same circumstances, above such ratio. On the other hand, the presence of a high concentration of water in the prepared product may be undesired, and thus a higher ratio than desirable for improved conversion is generally unwanted. If desired, excess water can be removed, e.g. by an evaporative technique, e.g. distillation, but the more water needs to be removed, the higher the energy consumption usually is for accomplishing removal or water to an intended maximum level. Accordingly, in particular in case the final product should contain little water or be essentially free of water, the weight to weight ratio of water to the compound to be hydrogenated (in particular phenol) fed into the reactor preferably is 0.05 or less, 0.02 or less, or 0.015 or less.

Regarding the minimum weight to weight ratio of water to the compound to be hydrogenated, it is observed that this minimum exceeds said ratio in the pure compound, which may comprise traces of that compound.

For instance, phenol may contain a trace of water, typically less than 200 ppm (see A. C. Dimian and C. S. Bildea: "Chemical Process Design, Computer-Aided Case Studies", Wiley-VCH Verlag GmbH&Co, KGaA, Mannheim, 2008, Chapter 5, page 130).

Usually, the weight to weight ratio of water to the compound to be hydrogenated—in particular phenol—on average is at least 0.0005, in particular 0.0010 or more, i.e. in the range of from 0.0010 to 0.10. In a preferred method of the invention, said ratio on average is at least 0.0015. In a particularly preferred method, for achieving improved conversion said ratio on average is at least 0.004. In a specific embodiment, said ratio is at least 0.010. A particularly preferred range of weight to weight ratio of water fed into the reactor to phenol fed into the reactor is in the range of from 0.0010 to 0.05, more in particular in the range of from 0.0015 to 0.02.

In particular the feeding of water may be beneficial in a method for hydrogenating an aromatic compound, such as phenol, wherein use is made of a supported catalyst comprising palladium and a support selected from the group of alumina and activated carbon.

The concentration of catalytic metal can be chosen within wide limits. Usually the catalytic metal is present in a concentration of 0.1-20 wt. %, based on the weight of the support, in particular in a concentration of 0.2-10 wt. % based on the weight of the support, more in particular in a concentration of 0.5-2 wt. % based on the weight of the support.

Specifically, in a method wherein water and the compound to be hydrogenated, in particular phenol, are fed into the reactor as a vapour, the concentration of catalytic metal, based on the weight of the support preferably is in the range of 0.1-10 wt. %, more preferably in the range of 0.2-5 wt. %, or in the range of 0.5-2 wt. %.

Specifically, in a method wherein water and compound to be hydrogenated, in particular phenol, are fed into the reactor as a liquid, the concentration of catalytic metal, based on the weight of the support preferably is in the range of 0.2-20 wt. %, more preferably in the range of 1-15 wt. %, or in the range of 5-10 wt. %.

As mentioned above, the supported catalyst comprises a dopant, in particular a dopant selected from the group of alkali metal hydroxides, alkaline earth metal hydroxides, alkaline earth metal oxides, carbonates of alkali metals and carbonates of alkaline earth metals. Specifically preferred are NaOH, KOH, sodium carbonates, and magnesium oxides.

Usually, the total dopant concentration usually is at least 0.5 wt. % based on the total weight of the catalyst (including support and catalytically active component). Preferably, the concentration is in the range of from 0.5 to 2 wt. %.

Other reaction conditions, including a hydrogen feed rate, temperature in the reactor and operating pressure, may be based on suitable conditions known in the art, per se, for instance on conditions described in the above cited prior art or prior art cited therein.

In a specifically preferred embodiment of the invention, phenol and water are fed into a slurry in the reactor in which the catalyst is present in a liquid phase comprising phenol and water. In yet another specifically preferred embodiment of the invention, phenol is fed into the reactor as a liquid and water is fed into the reactor as vapour.

The invention will now be elucidated by the following Comparative Experiments and examples without being limited thereto.

COMPARATIVE EXPERIMENT A

A gaseous mixture (total gas flow amounts to 27.0 Nl/hr) with a total pressure of 3.4 bar (absolute pressure), consisting of phenol (0.14 bar), hydrogen (0.61 bar) and nitrogen (balance), was continuously supplied to a tube reactor. The inner diameter of this tube reactor was 4.55 mm. The catalyst bed in this reactor consisted of a mixture of a phenol hydrogenation catalyst (: 0.2173 grams of 1 wt. % Pd on alumina support, with 1 wt. % Na (as $NaHCO_3$) added as promoter; BASF; sieve fraction between 0.2 and 1.0 mm, obtained after gentle crushing of the original star-shaped catalyst particles, followed by sieving) and 2.270 grams of inert SiC particles (particle size: 0.210-0.297 mm). The reactor was kept at a temperature of 170° C. After starting the experiment the conversion of phenol stabilized soon. After 29 hours of operation, the gaseous product flow leaving the reactor was analyzed and showed a phenol conversion of 40.92%. The major product formed was cyclohexanone. The selectivity towards cyclohexanol was 0.66%.

EXAMPLE 1

The experiment described in comparative experiment A was continued as described before with the exception that now also water was added to the gaseous feed of the reactor. The water concentration in the continuous feed of the reactor was 0.67 wt. % with respect to the phenol in the reactor feed. Almost directly after starting the dosing of water the conversion of phenol increased and stabilized soon at an increased level. After 29 hours of operation after starting the water dosing the gaseous product flow leaving the reactor was analyzed and showed a phenol conversion of 80.54%. The major product formed was cyclohexanone. The selectivity towards cyclohexanol was 1.02%. The high conversion of phenol could be continued during a long period of time.

COMPARATIVE EXPERIMENT B

The experiment described in Example 1 was continued without dosing of water to the feed of the reactor as described before with the exception that the reactor was kept at a temperature of 210° C. After one hour of operation under these modified conditions, the gaseous product flow leaving the reactor was analyzed and showed a phenol conversion of 40.92%. The major product formed was cyclohexanone. The selectivity towards cyclohexanol was 0.66%.

EXAMPLE 2

The experiment described in comparative experiment B was continued as described before with the exception that now also water was added to the gaseous feed of the reactor. The water concentration in the continuous feed of the reactor was 0.67 wt. % with respect to the phenol in the reactor feed. Almost directly after starting the dosing of water the conversion of phenol increased and stabilized soon at an increased level. After one hour of operation after starting the water dosing the gaseous product flow leaving the reactor was analyzed and showed a phenol conversion of 49.99%. The selectivity towards cyclohexanol was 1.32%.

COMPARATIVE EXPERIMENT C

The experiment described in comparative experiment A was repeated as described before, with the exception that in the amounts of phenol hydrogenation catalyst and inert SiC particles were 0.2202 grams and 2.30 grams, respectively.

After 45 hours of operation, the gaseous product flow leaving the reactor was analyzed and showed a phenol conversion of 36.26%. The major product formed was cyclohexanone. The selectivity towards cyclohexanol was 0.74%.

EXAMPLE 3

The experiment described in comparative experiment C was continued as described before with the exception that now also water was added to the gaseous feed of the reactor. The water concentration in the continuous feed of the reactor was 3.6 wt. % with respect to the phenol in the reactor feed. Almost directly after starting the dosing of water the conversion of phenol increased and stabilized soon at an increased level. After 4 hours of operation after starting the water dosing the gaseous product flow leaving the reactor was analyzed and showed a phenol conversion of 94.73%. The major product formed was cyclohexanone. The selectivity towards cyclohexanol was 1.46%.

COMPARATIVE EXPERIMENT D

The experiment described in Example 3 was continued without dosing of water to the feed of the reactor as described before with the exception that the reactor was kept at a temperature of 210° C. After one hour of operation under these modified conditions, the gaseous product flow leaving the reactor was analyzed and showed a phenol conversion of 18.90%. The major product formed was cyclohexanone. The selectivity towards cyclohexanol was 1.10%.

EXAMPLE 4

The experiment described in comparative experiment D was continued as described before with the exception that now also water was added to the gaseous feed of the reactor. The water concentration in the continuous feed of the reactor was 3.6 wt. % with respect to the phenol in the reactor feed. Almost directly after starting the dosing of water the conversion of phenol increased and stabilized soon at an increased level. After one hour of operation after starting the water dosing the gaseous product flow leaving the reactor was analyzed and showed a phenol conversion of 44.56%. The selectivity towards cyclohexanol was 1.26%.

COMPARATIVE EXPERIMENT E

The experiment described in comparative experiment A was repeated as described before with the exception that in this experiment intact (non-broken) catalyst particles were used. The filling of the tube reactor did consists of a bottom layer of 0.108 grams of inert SiC particles and 12 times one catalyst particle combined with 0.1885 grams of inert SiC. In total the catalyst bed in this reactor consisted of 0.2214 grams of phenol hydrogenation catalyst and 2.368 grams of inert SiC particles.

A gaseous mixture with a total pressure of 3.4 bar (absolute pressure), consisting of phenol (0.15 bar), hydrogen (0.60 bar) and nitrogen (balance), was continuously supplied to a tube reactor. The inner diameter of this tube reactor was 4.55 mm. The catalyst bed in this reactor consisted of a bottom layer of 0.108 grams of inert SiC particles and 12 times one phenol hydrogenation catalyst particle (: 0.9% Pd on alumina support, with 1 wt. % Na (as $NaHCO_3$) added as promoter; BASF) combined with 0.1885 grams of inert SiC particles (particle size: 0.210-0.297 mm). In total the catalyst bed in this reactor consisted of 0.2214 grams of phenol hydrogenation catalyst and 2.368 grams of inert SiC particles.

The reactor was kept at a temperature of 170° C. After starting the experiment the conversion of phenol stabilized soon. After 26 hours of operation, the gaseous product flow leaving the reactor was analyzed and showed a phenol conversion of 29.80%. The major product formed was cyclohexanone. The selectivity towards cyclohexanol was 4.91%.

EXAMPLE 5

The experiment described in comparative experiment E was continued as described before with the exception that now also water was added to the gaseous feed of the reactor. The water concentration in the continuous feed of the reactor was 0.67 wt. % with respect to the phenol in the reactor feed. Almost directly after starting the dosing of water the conversion of phenol increased and stabilized soon at an increased level. After 26 hours of operation after starting the water dosing the gaseous product flow leaving the reactor was analyzed and showed a phenol conversion of 49.07%. The major product formed was cyclohexanone. The selectivity towards cyclohexanol was 6.37%.

COMPARATIVE EXPERIMENT F

In a commercial phenol hydrogenation plant a gaseous mixture with a total pressure of 3.6 bar (absolute pressure) was continuously supplied to a shell and tubes heat exchanger reactor with a catalyst in tubes and raising steam outside. The inner diameter of each tube was 25 mm. Each tube is filled with hydrogenation catalyst (1 wt. % Pd on alumina support, with 1 wt. % Na (as $NaHCO_3$) added as promoter; BASF). The height of the catalyst bed in each reactor tube is 2.4 m. The pressure of the produced steam was 6.5 bar.

The total gas flow that is fed into the reactor amounts to 16150 $Nm^3$/hr consisting of mainly hydrogen (about 70 vol. %), phenol (about 7200 kg/hr) and inert components (like $CH_4$).

Analysis of the product flow leaving the reactor showed that 87.2 mol % of the phenol that was fed into the reactor was converted into cyclohexanone (76.2 mol %) and cyclohexanol (11.0 mol %).

EXAMPLE 6

The experiment described in comparative experiment F was continued as described before with the exception that now also 100 kg/hr water was added to the gaseous feed of the reactor. The ratio of water to phenol in the continuous feed of the reactor equals to ca. 1.4 wt. %. Almost directly after starting the dosing of water the conversion of phenol increased and stabilized soon at an increased level. After 3 hours of operation after starting the water dosing the gaseous product flow leaving the reactor was analyzed.

This analysis showed that 98.1 mol % of the phenol that was fed into the reactor was converted into cyclohexanone (87.9 mol %) and cyclohexanol (10.2 mol %).

The invention claimed is:

1. A method for preparing cyclohexanone, cyclohexanol or a mixture thereof in a continuous process, the process comprising:
   (a) feeding phenol to a reactor comprising a hydrogenation catalyst;
   (b) catalytically hydrogenating the phenol fed into the reactor in the presence of the hydrogenation catalyst, wherein the hydrogenation catalyst is a supported catalyst comprising a dopant selected from the group consisting of alkali metal hydroxides, alkaline earth metal hydroxides, alkaline earth metal oxides, carbonates of alkali metals and carbonates of alkaline earth metals; and
   (c) continuously or intermittently feeding water into the reactor during hydrogenation of the phenol according to step (a) at an average weight to weight ratio of water fed into the reactor to phenol fed into the reactor of 0.10 or less.

2. The method according to claim 1, wherein step (c) is practiced such that the water is fed into the reactor in a weight to weight ratio of water fed into the reactor to phenol fed into the reactor in the range of from 0.0010 to 0.10.

3. The method according to claim 2, wherein step (c) is practiced such that the water is fed into the reactor in a weight to weight ratio of water fed into the reactor to phenol fed into the reactor in the range of from 0.0010 to 0.05.

4. The method according to claim 3, wherein step (c) is practiced such that the water is fed into the reactor in a weight to weight ratio of water fed into the reactor to phenol fed into the reactor in the range of from 0.0015 to 0.02.

5. The method according to claim 1, which comprises feeding each of the phenol and water into the reactor as a vapour.

6. The method according to claim 1, which comprises feeding each of the phenol and water into the reactor as a liquid.

7. The method according to claim 1, which comprises feeding the phenol into the reactor as a liquid and feeding the water into the reactor as vapour.

8. The method according to claim 1, wherein the catalyst is a supported catalyst comprising a support selected from the group consisting of alumina, activated carbon, titanium oxide, calcium carbonate and carbon black.

9. The method according to claim 1, wherein the hydrogenation catalyst comprises at least one catalytic metal selected from the group consisting of palladium, platinum, ruthenium, rhodium, iridium, rubidium and osmium.

10. The method according to claim 9, wherein the hydrogenation catalyst comprises at least one catalytic metal selected from the group consisting of palladium and platinum.

11. The method according to claim 10, wherein the catalyst comprises palladium and a support selected from the group consisting of alumina and activated carbon.

12. The method according to claim 9, wherein the catalytic metal is present in a concentration of 0.1-20 wt. %, based on the weight of the support.

13. The method according to claim 1, wherein step (a) comprises hydrogenating the phenol in a shell and tubes heat exchange reactor.

14. The method according to claim 8, which comprises feeding each of the phenol and water into a slurry in the reactor in which the catalyst is present in a liquid phase comprising phenol and water.

15. The method according to claim 12, wherein the catalytic metal is present in a concentration of 0.2-10 wt. % based on the weight of the support 16. The method according to claim 12, wherein the catalytic metal is present in a concentration of 0.5-2 wt. % based on the weight of the support.

* * * * *